United States Patent
Cole

(10) Patent No.: US 7,179,651 B1
(45) Date of Patent: Feb. 20, 2007

(54) CENTRIFUGAL SAMPLE EVAPORATOR WITH DIRECT-HEAT SHIELD AND UNIFORM HEATING

(75) Inventor: Michael Cole, Saxmundham (GB)

(73) Assignee: Genevac Limited (GB)

( * ) Notice: Subject to any disclaimer, the term of this patent is extended or adjusted under 35 U.S.C. 154(b) by 271 days.

(21) Appl. No.: 10/030,611

(22) PCT Filed: Jul. 7, 2000

(86) PCT No.: PCT/GB00/02624

§ 371 (c)(1),
(2), (4) Date: Apr. 15, 2002

(87) PCT Pub. No.: WO01/04600

PCT Pub. Date: Jan. 18, 2001

(30) Foreign Application Priority Data

Jul. 9, 1999 (GB) ................................. 9916028.5
Dec. 22, 1999 (GB) ................................. 9930157.4

(51) Int. Cl.
*G01N 35/00* (2006.01)

(52) U.S. Cl. ......................... 436/45; 422/99; 422/100; 422/101; 422/102; 422/64; 436/180; 436/177

(58) Field of Classification Search ................. 422/72, 422/161, 99–102, 64; 436/45, 177, 180
See application file for complete search history.

(56) References Cited

U.S. PATENT DOCUMENTS

| | | | | |
|---|---|---|---|---|
| 4,226,669 A | | 10/1980 | Vilardi ........................ | 159/6 R |
| 4,832,678 A | * | 5/1989 | Sheeran ....................... | 494/16 |
| 5,167,926 A | * | 12/1992 | Kimura et al. ................. | 422/67 |
| 5,217,572 A | * | 6/1993 | Guy et al. .................... | 159/6.1 |
| 5,356,365 A | * | 10/1994 | Brierton ...................... | 494/14 |
| 5,431,620 A | | 7/1995 | Schenck ....................... | 494/7 |

* cited by examiner

*Primary Examiner*—Jill Warden
*Assistant Examiner*—Jyoti Nagpaul
(74) *Attorney, Agent, or Firm*—Barnes & Thornburg LLP

(57) ABSTRACT

A sample holder is described, for use in centrifugal evaporators, which permits accelerated evaporation of solvents from samples while ensuring that samples from which evaporation is complete are not damaged by overheating. The sample holder is radiantly heated and has sample containers mounted either directly in it, or in intermediate holders themselves mounted in it. The sample holder imparts heat to the samples and has a cross-sectional area chosen such that no appreciable temperature gradient exists between the radiantly or otherwise heated surfaces of the holder and the sample containers. The sample containers are mounted in the holder at an angle between 35° and 65° to the vertical and orientated such that centrifugal force tends to retain the sample material in the containers. The sample holder may be combined with other holders in a stack, the joints between adjacent holders in the stack being adapted to minimize the temperature difference across them.

14 Claims, 3 Drawing Sheets

CENTRIFUGAL SAMPLE EVAPORATOR WITH DIRECT-HEAT SHIELD AND UNIFORM HEATING

FIELD OF THE INVENTION

This invention concerns centrifugal evaporators, which are used to evaporate solvents containing dissolved material, so as to recover the latter in a dry condition.

BACKGROUND TO THE INVENTION

There are occasions on which such material is dissolved in different solvents, (or in mixtures of two or more solvents in different proportions), and is to be recovered by simultaneous evaporation of the solvents. One example is the output from a preparative HPLC machine. Where material has been dissolved in a composite solvent having two or more components which vary in proportion from one sample to another (e.g. water and acetonitrile in varying proportions), the solvent can vary in the example given from almost pure water to almost pure acetonitrile. Acetonitrile is more volatile than water and has a lower heat of vaporisation so that it evaporates faster in a centrifugal evaporator leading to differential sample masses during evaporation. This leads to two problems.

Firstly out of balance loads can be generated. Various techniques have been proposed to deal with this first problem.

Secondly there is the possibility of overheating samples which dry before others. This can arise where material is dissolved in solvent mixtures containing a higher proportion of the more volatile component than in other samples. In this situation continued heating of the samples to complete the evaporation of the solvent mixtures containing a higher proportion of the less volatile component can result in the dried material becoming overheated. Samples that are still evaporating will not rise above the temperature of the evaporating liquid, but any dry samples can reach temperatures which are high enough to cause damage to the residue material if precautions are not taken to protect that material.

Figure 1:
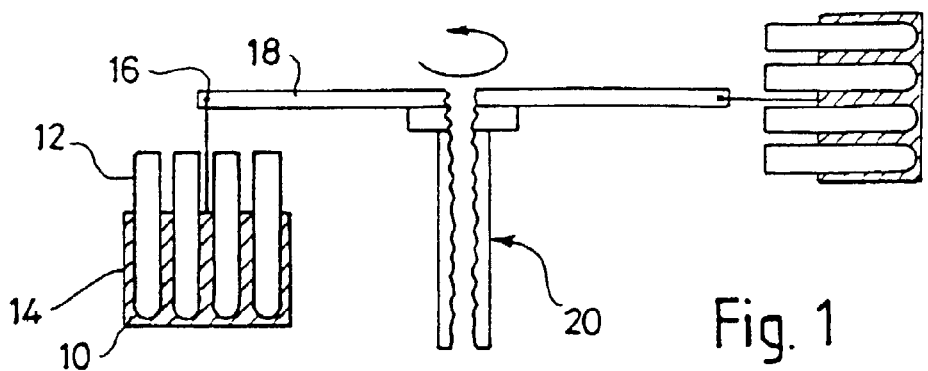

In one arrangement designed to try and overcome this problem, it has been proposed to mount sample containers in four or more aluminium blocks in swinging buckets in an evaporator, as illustrated in FIG. 1. Here the aluminium block is denoted by reference numeral 10, and one of the sample containers by 12. The block is located in a bucket 14 which is free to swing about a pivot 16 so that when the rotor 18 is stationary the buckets hang vertically as shown on the left hand side of FIG. 1. When the rotor 18 spins up to speed by rotating the vertical shaft 20, the buckets swing upwardly and outwardly from the position shown on the left hand side of FIG. 1, and take up a horizontal position under the influence of centrifugal force, as shown on the right hand side of FIG. 1.

Overheating is prevented by sensing the temperature of one of the blocks and controlling the heat input to the rotating assembly so as to maintain the temperature at or below the maximum permissible dry material temperature. Provided the distribution of differing solvent mixtures throughout all the samples in all the blocks is uniform (which unfortunately cannot be guaranteed), this may protect any samples that become dry. But in cases in which the material is dissolved in solvent mixtures of randomly variable composition (as is more often the case), a block which is not temperature controlled, may contain relatively more samples containing a high proportion of the more volatile component, and all the samples in it may become dry, while samples in the block whose temperature is being controlled may still contain solvent. In those circumstances the block whose temperature is not being controlled, may rise in temperature to a value at which damage can occur to the dry residue sample material therein.

This problem could be overcome by incorporating a temperature sensor in every sample block, and controlling the heat to each block independently so as to keep each block below the maximum permissible temperature. However this can be expensive and difficult to implement especially if there are a large number of sample blocks.

OBJECT OF THE INVENTION

It is an object of the present invention to enable heat to be provided to enhance the evaporation rate of samples of different composition, especially differing solvent composition, which can therefore exhibit different evaporation rates, without allowing samples which dry faster to become overheated if they become dry, while heat is still being supplied to dry samples which evaporate more slowly.

SUMMARY OF THE INVENTION

According to one aspect of the present invention a sample holder for use in centrifugal evaporators that include heating means to assist in the evaporation process, is formed from a material having high thermal conductivity and is adapted to receive containers each containing a sample to be evaporated, and the containers are mounted in the holders so that neither the sample containers nor their contents can receive heat directly from the heating means, but only from the holder.

In one embodiment the sample holder comprises a block of material having high thermal conductivity, a preferred material for which is aluminium.

Preferably the cross-section of the sample holder is selected to ensure that no appreciable temperature gradients exist in use anywhere in the sample holder.

The sample containers may be mounted directly in the high conductivity material block, or in intermediate holders which are mounted in recesses in the block.

In a single layer evaporator it is feasible to make the sample holder from a single block of high conductivity material. Although it is possible to do this in a multi layer evaporator, it is inconvenient and expensive to do so, and the sample holder in a multi-layer evaporator is preferably made of several sample holders joined by spacing members in such a way as to minimise any temperature difference between adjoining sample holders.

Preferably the sample holders and spacing members have cross-sections chosen so as to keep thermal gradients within the whole structure to a very low value.

Preferably, during evaporation, temperature variation over the whole structure should be less than 1° C.

Preferably the sample containers are held rigidly at a fixed angle to the vertical. Preferably the fixed angle lies between 35° and 65°.

The invention also lies in a centrifugal evaporator incorporating a sample holder as set out in the foregoing description.

The invention also lies in a method of heating samples in a centrifugal evaporator, comprising the steps of mounting the samples in good thermal contact with a mass of high thermal conductivity material which forms a sample holder, and supplying energy to heat the sample holder and in turn the samples wherein the sample holder shields the samples from direct heat energy, whereby the samples receive no heat directly, but only via the mass of high thermal conductivity material forming the sample holder.

The invention also lies in a method of controlling the heating of samples in a centrifugal evaporator to assist in evaporation of solvent therefrom, in which the samples are situated in containers, which are located in a sample holder as aforesaid, and the temperature of the latter is monitored.

The invention also lies in a method of preventing dry sample material from damage by overheating as energy is supplied to evaporate solvent in other samples, in which the samples are contained in containers, which are located in a sample holder as aforesaid, and the sample containers are shielded from direct heat energy by the sample holder material, and the temperature of the latter is monitored and the heat energy is reduced or cut off if the temperature of the holder rises above a predetermined maximum.

The invention will now be described with reference to FIGS. 1, 3(a) and 3(b) which show sample holders such as may be used in centrifugal evaporators, and by way of example, with reference to the remaining FIGS. 2, 4, 5 and 6 of the accompanying drawings.

As previously mentioned, FIG. 1 shows an earlier proposal to try and overcome the problem of overheating samples which dry earlier than others in the same batch.

Figure 3A:
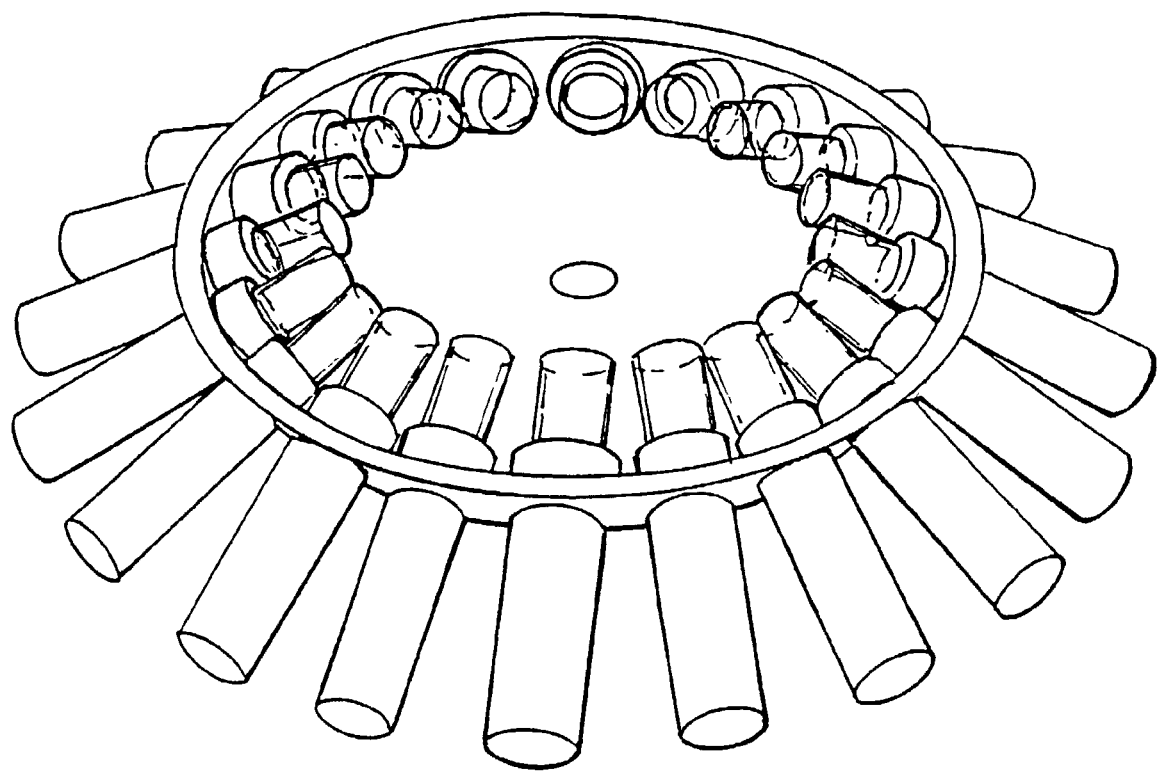

FIG. 3a shows a known form of sample holder made from aluminium, wherein sample containers (typically glass tubes) are located in tubular sleeves (which may also be formed from metal, possibly also aluminium) which are supported around a rim of a shallow dish having a thin cross-section. An external source supplies heat to the sleeves and the samples therein, but the sleeves are only thermally linked by the thin cross-section of the rim, which even if formed from aluminium, can still allow a significant temperature gradient to exist between one sleeve and another around the rim.

Dried samples therefore can rise considerably in temperature relative to adjoining samples which will contain liquid (and therefore remain at a lower temperature in the presence of solvent if heating is continued to dry samples in which solvent remains. Such rises in temperature can result in overheating of the dried samples and damage thereto.

Figure 3B:
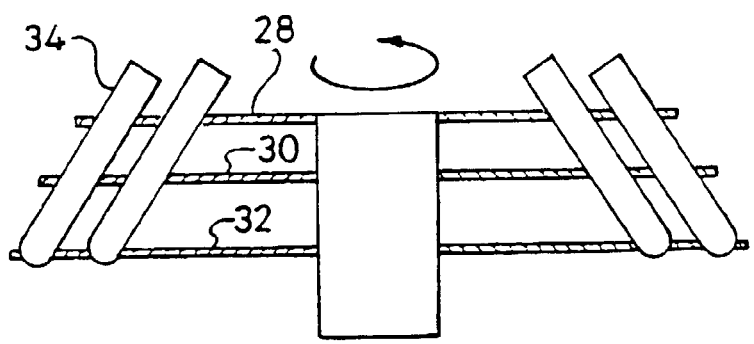

Other angled sample holders have been made of a series of separated plates 28, 30 and 32 such as shown in FIG. 3b. Here the plates have elliptical holes to receive the sample tubes 34, which are thereby held in a similar angled relation to the vertical.

Neither of these forms of construction prevents heat from reaching the tubes directly nor addresses the problem of overheating samples which dry before others.

Figure 2:
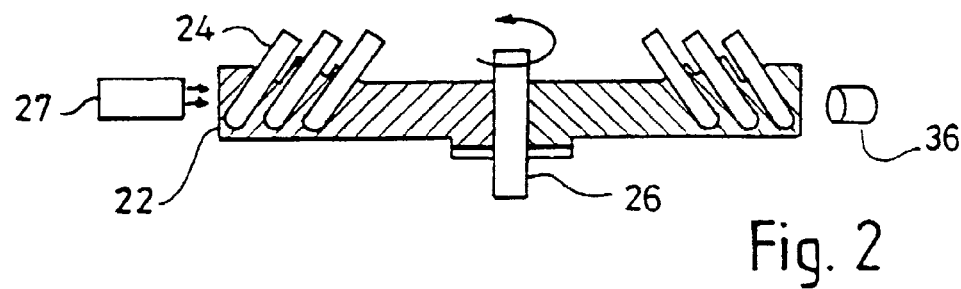

A preferred embodiment of the invention is illustrated in FIG. 2. A block of solid aluminium 22 has a plurality of 45° angled holes in which tubes 24 containing the samples are a snug fit, and are thereby held at an angle of 45° to the vertical shaft 26.

The block 22 carrying the sample containing tubes 24 is rotated by the vertical shaft 26 in a chamber (not shown) and the latter is evacuated in known manner for centrifugal evaporators. Radiant heat is applied to the outer edge of the aluminium block 22 by a heater 27. The presence of the aluminium prevents radiation from reaching the sample containing tubes directly.

In a similar manner the underside of the block 22 may be heated in addition to, or instead of, the outer edge, by a heating means, (not shown) suitably positioned relative to the block.

Two or more heaters such as 27 may be positioned around the block 22, in place of a single heater as shown. Likewise the, or each, heater may take any convenient form and may for example comprise one or more sources of radiant heat energy, or microwave energy, or an RF induction coil may extend substantially therearound.

An optical pyrometer 36 senses the temperature of the block remotely through a window in the vacuum chamber wall. Alternatively a temperature sensor may be mounted in or on the block with means to transmit signals containing temperature information to a receiver outside the vacuum chamber. Decoding the pyrometer output, or signals from the remote receiver, may be used to generate signals to control the operation of the heater(s) so as to maintain the temperature of the block(s) at high enough value, to allow rapid solvent evaporation, but below that at which damage will occur to the sample material. This is achieved since even when the contents of a tube become completely dry, the tube and its now dry residue content still cannot exceed the temperature of the aluminium block, and by controlling the heat energy with reference to the block temperature, so any dried sample material will be protected.

Figure 4:
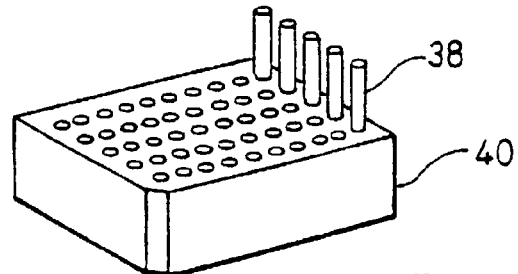
Figure 5:
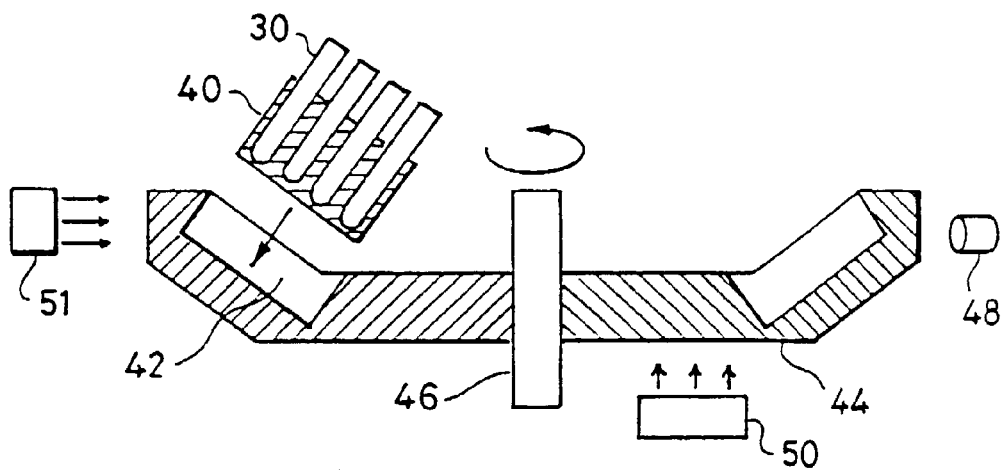

Another embodiment is shown in FIGS. 4 and 5. Here sample tubes 38 are carried snugly in openings in intermediate aluminium blocks 40, one of which is illustrated in FIG. 4. The intermediate blocks are fitted into recesses 42 in the main rotatable block 44, so as to angle the sample tubes at between 35° and 65°, typically 45°, to the axis of the vertical shaft 46.

The main block 44, with intermediate blocks 40 in place, is then spun up to speed and subjected to vacuum, while heat is directed to the underside of the main aluminium block, as illustrated by heater 50, (or to an edge thereof by an alternatively located heater 51). The temperature of the main block 44, and therefore the maximum temperature of the intermediate blocks 40, is monitored and in turn controlled, using signals from an optical pyrometer 48, and a temperature control system, such as described above in relation to FIG. 2.

Figure 6:
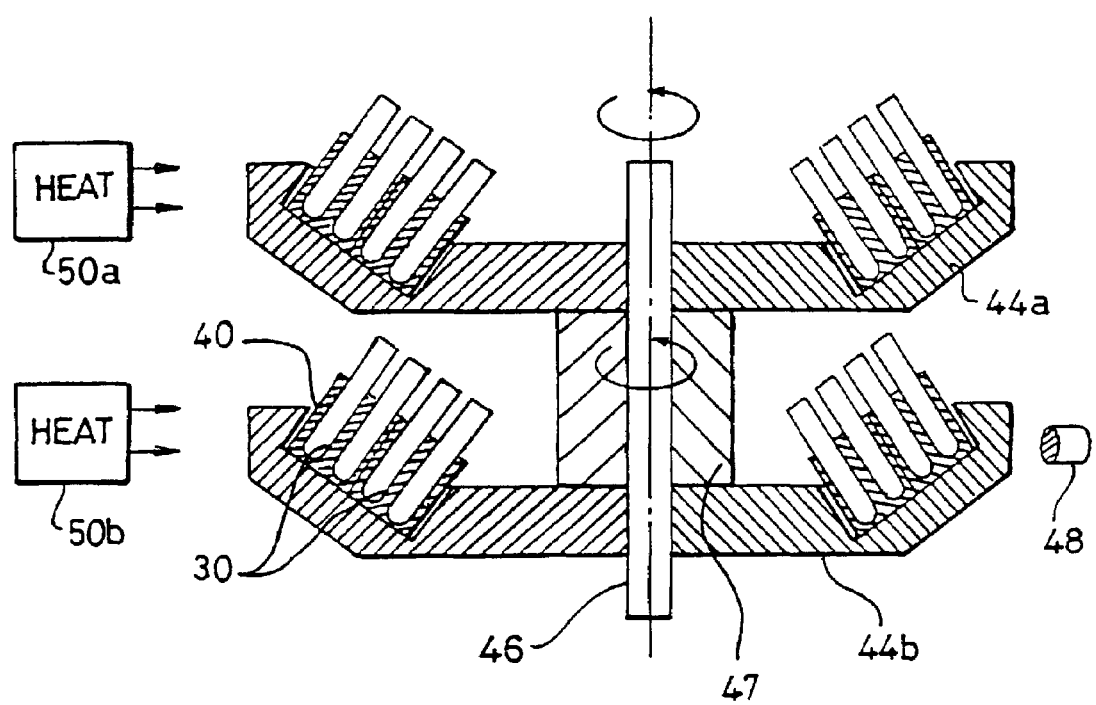

FIG. 6 shows a development of the arrangement shown in FIG. 5, in which the blocks 40 are mounted in two trays 44a and 44b, which form two layers of a composite assembly. Each layer comprising blocks 40 and tubes 30. The trays are carried on, and spaced apart (vertically), a shaft 46. A solid aluminium spacer 47 is located therebetween in good thermal contact with each of the trays. Heat is supplied by means of two radiation sources 50a and 50b, (although one heat source may be sufficient and if desired, more than two could be used). An optical pyrometer 48 monitors the temperature of one of the layers. By selecting the spacer 47 to have sufficient mass and sufficiently good thermal contact with the two layers, both the latter will remain at substantially the same temperature in use, so that by controlling the heat input to one and thereby ensuring its temperature does not exceed a safe value, so the other will also be maintained at a safe temperature, in relation to any dried sample material thereon.

The invention claimed is:

1. A sample holder for centrifuging samples in centrifugal evaporators that include heating means to assist the evaporation process, wherein the sample holder is formed from a material having high thermal conductivity, and is adapted to receive containers each containing a sample to be evaporated, and the containers are mounted in the holder, so that neither the latter sample containers nor their contents can receive radiant heat directly from the heat source during centrifuging of the samples in the sample holder, but only from the holder, wherein the sample containers are held at a fixed angle to the vertical between 35° and 65° and orientated such that the force exerted on the contents when the centrifugal evaporator rotates them tends to retain the contents in the containers.

2. A sample holder according to claim 1 which is in the form of a block of high thermal conductivity material.

3. A sample holder according to claim 1 which is formed from aluminium.

4. A sample holder according to claim 1 of which the cross-section is selected so that in use no appreciable temperature gradients exist therein during evaporation.

5. A sample holder according to claim 1 having sample containers mounted directly therein.

6. A sample holder according to claim 1 in which the sample containers are mounted in one or more intermediate holders which in turn are mounted in recesses in the sample holder.

7. A centrifugal evaporator comprising a vacuum chamber and drive means coupled to the vacuum chamber, the vacuum chamber containing heating means and a sample holder according to claim 1, the drive means being operable to rotate the sample holder in the vacuum chamber and the heating means being operable to supply heat to the sample holder.

8. A sample holder for centrifuging samples in centrifugal evaporators that include heating means to assist the evaporation process, wherein the sample holder is formed from a material having high thermal conductivity, and is adapted to receive containers each containing a sample to be evaporated, and the containers are mounted in the holder, so that neither the latter sample containers nor their contents can receive radiant heat directly from the heat source during centrifuging of the samples in the sample holder, but only from the holder, said holder being in combination with at least one other sample holder to form a stack with a spacing member between adjoining holders in good thermal contact therewith, so that the temperature of one holder will tend to be the same as the temperature of the other.

9. A sample holder according to claim 8 which is in the form of a block of high thermal conductivity material.

10. A sample holder according to claim 8 which is formed from aluminium.

11. A sample holder according to claim 8 of which the cross-section is selected so that in use no appreciable temperature gradients exist therein during evaporation.

12. A sample holder according to claim 8 having sample containers mounted directly therein.

13. A sample holder according to claim 8 in which the sample containers are mounted in one or more intermediate holders which in turn are mounted in recesses in the sample holder.

14. A centrifugal evaporator comprising a vacuum chamber and drive means coupled to the vacuum chamber, the vacuum chamber containing heating means and a sample holder according to claim 8, the drive means being operable to rotate the sample holder in the vacuum chamber and the heating means being operable to supply heat to the sample holder.

* * * * *